United States Patent
Leinekugel Le Cocq et al.

(10) Patent No.: US 8,658,848 B2
(45) Date of Patent: Feb. 25, 2014

(54) HIGHLY FLEXIBLE PROCESS AND APPARATUS FOR THE SIMULATED COUNTER-CURRENT PRODUCTION OF PARA-XYLENE

(75) Inventors: Damien Leinekugel Le Cocq, Lyons (FR); Philibert Leflaive, Mions (FR); Luc Wolff, Chaponnay (FR); Gerard Hotier, Rueil Malmaison (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/593,819

(22) Filed: Aug. 24, 2012

(65) Prior Publication Data
US 2013/0053610 A1    Feb. 28, 2013

(30) Foreign Application Priority Data
Aug. 26, 2011    (FR) ..................... 11 02604

(51) Int. Cl.
*C07C 7/12*    (2006.01)
(52) U.S. Cl.
USPC ........... 585/828; 585/820; 585/825; 585/826; 585/827
(58) Field of Classification Search
None
See application file for complete search history.

(56) References Cited

U.S. PATENT DOCUMENTS

| | | | |
|---|---|---|---|
| 6,063,285 A | 5/2000 | Hotier et al. | |
| 8,329,975 B2* | 12/2012 | Pieper et al. | 585/820 |
| 2007/0149841 A1* | 6/2007 | Lee et al. | 585/826 |
| 2008/0149565 A1* | 6/2008 | Lee et al. | 210/663 |
| 2009/0234170 A1* | 9/2009 | Lee et al. | 585/470 |
| 2011/0315634 A1* | 12/2011 | Hotier et al. | 210/659 |

FOREIGN PATENT DOCUMENTS

| | | |
|---|---|---|
| EP | 0 960 642 A1 | 12/1999 |
| EP | 1 525 040 A2 | 4/2005 |
| WO | WO 2004/013075 A1 | 2/2004 |
| WO | WO 2004/018072 A2 | 3/2004 |

OTHER PUBLICATIONS

Search Report of FR 1102604 (Mar. 20, 2012).

\* cited by examiner

*Primary Examiner* — Tam M Nguyen
(74) *Attorney, Agent, or Firm* — Millen, White, Zelano & Branigan, P.C.

(57) ABSTRACT

A process for the production of para-xylene by simulated counter-current adsorption with high flexibility with respect to a reference run (100%) uses 2 adsorbers each with 12 beds, said adsorbers being able to be connected in accordance with 3 different modes; the flexibility obtained is 50% to 150%.

15 Claims, 4 Drawing Sheets

HIGHLY FLEXIBLE PROCESS AND APPARATUS FOR THE SIMULATED COUNTER-CURRENT PRODUCTION OF PARA-XYLENE

1. FIELD OF THE INVENTION

The invention relates to the field of separating para-xylene from other aromatic C8 isomers. To carry out such separation, a family of processes and associated devices is used, which is known under the name of simulated moving bed separation processes or simulated counter-current separation, or as the VARICOL process; we shall hereinafter use the general term of SCC (abbreviation of simulated counter-current) separation processes.

PRIOR ART

SCC separation is well known in the art. As a general rule, a para-xylene separation process functioning in simulated counter-current mode comprises at least four zones, and possibly five or six, each of those zones being constituted by a certain number of successive beds, and each zone being defined by its position included between a supply point and a withdrawal point. Typically, a SCC unit for the production of para-xylene is supplied by at least one feed F to be fractionated (containing para-xylene and the other aromatic C8 isomers) and a desorbant D, occasionally termed the eluent (generally para-diethylbenzene or toluene), and from said unit at least one raffinate R containing the isomers of para-xylene and desorbant and an extract E containing para-xylene and desorbant are withdrawn. Distillation columns can be used to separate the desorbant from the raffinate and the desorbant from the extract, the desorbant being re-introduced into the SCC unit.

Other injection-withdrawal points may be added in order to rinse the distribution circuits, as described, for example, in U.S. Pat. No. 7,208,651. Adding such supplemental rinsing streams does not in any way change the principle of the function of the SCC; for the sake of brevity, we shall not add these supplemental injection and withdrawal points to the description of the process of the invention.

The supply and withdrawal points are modified over time, shifted in the same direction by a value corresponding to one bed. The various injection or withdrawal points may be shifted either simultaneously or non-simultaneously, as disclosed in U.S. Pat. No. 6,136,198. The process in accordance with this second functional mode is known as the "Varicol" process.

Conventionally, four different chromatographic zones are defined in a SCC unit:
  zone 1: zone for desorbant of the compounds of the extract, included between the injection of desorbant D and the removal of extract E;
  zone 2: zone for desorbant of the compounds of the raffinate, included between the removal of the extract E and the injection of the feed to be fractionated F;
  zone 3: zone for adsorption of the compounds of the extract, included between the injection of the feed and the withdrawal of the raffinate R;
  zone 4: zone located between the withdrawal of the raffinate and the injection of the desorbant.

The prior art describes in detail various devices and processes for carrying out the separation of feeds in SCC.

Particular patents that may be cited are U.S. Pat. No. 2,985,589, U.S. Pat. No. 3,214,247, U.S. Pat. No. 3,268,605, U.S. Pat. No. 3,592,612, U.S. Pat. No. 4,614,204, U.S. Pat. No. 4,378,292, U.S. Pat. No. 5,200,075 and U.S. Pat. No. 5,316,821. These patents also describe the function of a SCC in detail.

As described by Lim et al (2010, Ind Eng Chem Res, vol 49, p 3316-3327), the process for the separation of para-xylene by SCC is generally composed of 24 beds, distributed among 2 adsorbers each containing 12 beds. The 2 adsorbers are connected in series, and the SCC cycle thus comprises 24 steps during which each stream (D, E, F, R) is injected or withdrawn downstream of each of the 24 beds.

The term "connection in series" for the two adsorbers of twelve beds means the following 3 features:
  the twelfth bed of the first adsorber is connected to the first bed of the second adsorber via a line containing at least one recirculation pump and possibly other equipment such as a flow meter, a pressure sensor, etc.;
  the twelfth bed of the second adsorber is connected to the first bed of the first adsorber via a line containing at least one recirculation pump and possibly other equipment such as a flow meter, a pressure sensor, etc.;
  the assembly of the two adsorbers has 1 point for introducing feed, 1 point for introducing desorbant, 1 point for withdrawing raffinate and 1 point for withdrawing extract.

The pressure drops occurring in a SCC process are directly linked to the interstitial velocities of the fluid phase in the beds of adsorbent.

The term "interstitial velocity" means the actual velocity of fluid between the particles constituting the solid adsorbent. The pressure drops play an important role in sizing the recirculation pump or pumps, the thickness of the adsorber walls, the size of the support systems for the distributor plates, the mechanical behaviour of the grains of adsorbent, etc.

The interstitial velocity may also play a very important role as regards the mechanical behaviour of the grains of adsorbent and may even become a limiting factor in operating a SCC unit.

It is known from the prior art (in particular from U.S. Pat. No. 7,649,124 and U.S. Pat. No. 7,635,795) that the process for the production of para-xylene by SCC has a limited productivity. Solutions have been proposed in the prior art to improve this process:
  patents FR 2 743 068 and U.S. Pat. No. 7,635,795 present processes using several adsorption steps. The first step is intended to produce a stream enriched in para-xylene with a purity insufficient to allow it to be used commercially (less than 99% by weight). The second step can be used to obtain very high purity para-xylene. In particular, FIG. 5 of U.S. Pat. No. 7,635,795 illustrates the debottlenecking of a pre-existing unit by 24-bed SCC by adding an adsorber for pre-treatment of the feed;
  patents FR 2 693 186, FR 2 757 507 and U.S. Pat. No. 7,649,124 present processes using a step for SCC adsorption in combination with crystallization. The first step is intended to produce, by SCC, a stream enriched in para-xylene with a purity which is insufficient to allow it to be used commercially (typically of the order of 90% by weight). The second step can be used to obtain very high purity para-xylene by crystallization. In particular, FIG. 5 of U.S. Pat. No. 7,649,124 illustrates the debottlenecking of a pre-existing unit by 24-bed SCC (composed of two 12-bed adsorbers) by means of a modification to an adsorption process using two adsorbers in parallel and adding a crystallization step to post-treat the extracts.

All of the solutions recommended in the prior art to solve the problem of limiting the production of units for the production of para-xylene using a 24-bed simulated moving bed thus consists of adding a separation stage (an adsorber to pre-treat the feed and/or a post-treatment of the extract by crystallization), giving rise to very substantial costs.

A process for the production of para-xylene by SCC also has limitations as regards the minimum quantity of feed to be treated. In fact, when the flow rates in the unit are very low, the hydrodynamic conditions for good operation of the distributor plates and associated networks are no longer satisfied, inducing a loss of purity and/or yield.

Thus, prior art processes for the production of para-xylene by SCC are of low flexibility vis-á-vis a variation in the flow rate of the feed to be treated. In some cases, such as in the case of a problem in the supply of the feed, maintenance of the reforming unit or of a toluene transalkylation unit with aromatic compounds containing at least 9 carbon atoms, the processes for the production of para-xylene by SCC have to be able to process low feed flow rates.

Further, a maintenance operation on one of the constituent elements of a process for the production of para-xylene by SCC necessitates complete stoppage of the process.

The process of the invention is intended to overcome the problem of variation in the flow rate of the feed to be treated by providing for optimized use of all or a portion of the beds of adsorbent of the SCC process in order to produce high purity (i.e. more than 99.7% pure) para-xylene directly.

A further aim of the invention is to be able to maintain a production of high purity (i.e. more than 99.7% pure) para-xylene during certain maintenance operations on an adsorber, meaning that the use of a portion of the beds of adsorbent is optimized.

The two adsorbers are associated in series such that the device functions in a single 24-step cycle. There is one feed injection point (F), one desorbant introduction point (D), one extract withdrawal point (E) and one raffinate withdrawal point (R).

Figure 3:
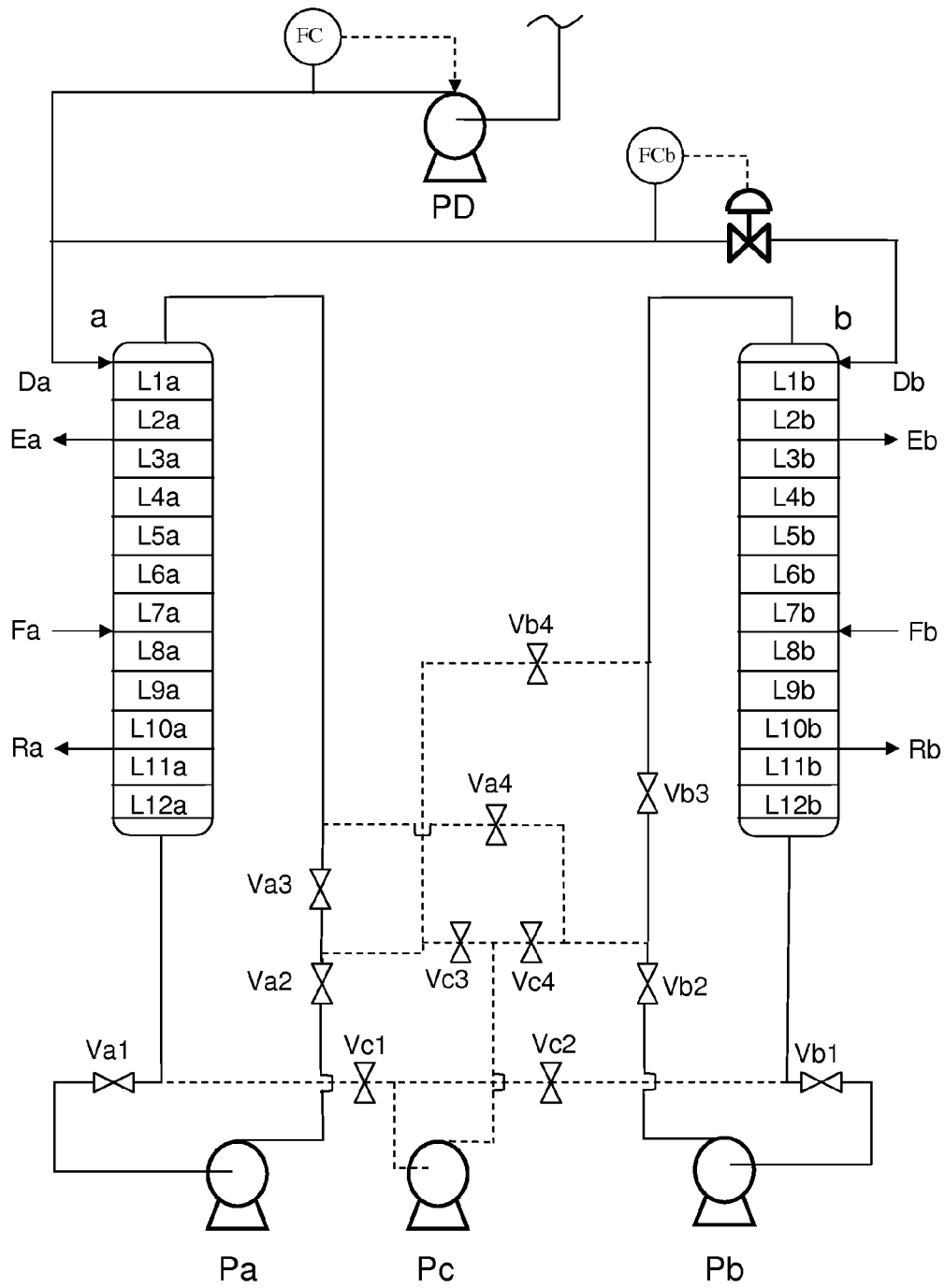

FIG. 3 represents the device of the invention, constituted by two adsorbers (a) and b) each with 12 beds (L1a to L12a for adsorber a), and L1b to L12b for adsorber b), functioning in "high productivity" mode. The two adsorbers are decoupled and carry out 2 cycles of 12 steps in parallel. For each adsorber, there is injection of a stream of feed (Fa for adsorber a), and Fb for adsorber b), of a stream of desorbant (Da for adsorber a), and Db for adsorber b), withdrawing a stream of extract (Ea for adsorber a) and Eb for adsorber b) and of a stream of raffinate (Ra for adsorber a) and Rb for adsorber b). The recirculation pump for adsorber a) is denoted Pa and the recirculation pump for adsorber b) is denoted Pb. The single replacement pump for the recirculation pumps is denoted Pc. The set of valves (Vc1 to Vc4) and the dashed lines (corresponding to lines which are not used when the replacement pump Pc is not in use) means that the pump Pc can be used either in place of pump Pa of adsorber a) or in place of pump Pb of adsorber b).

Figure 4:
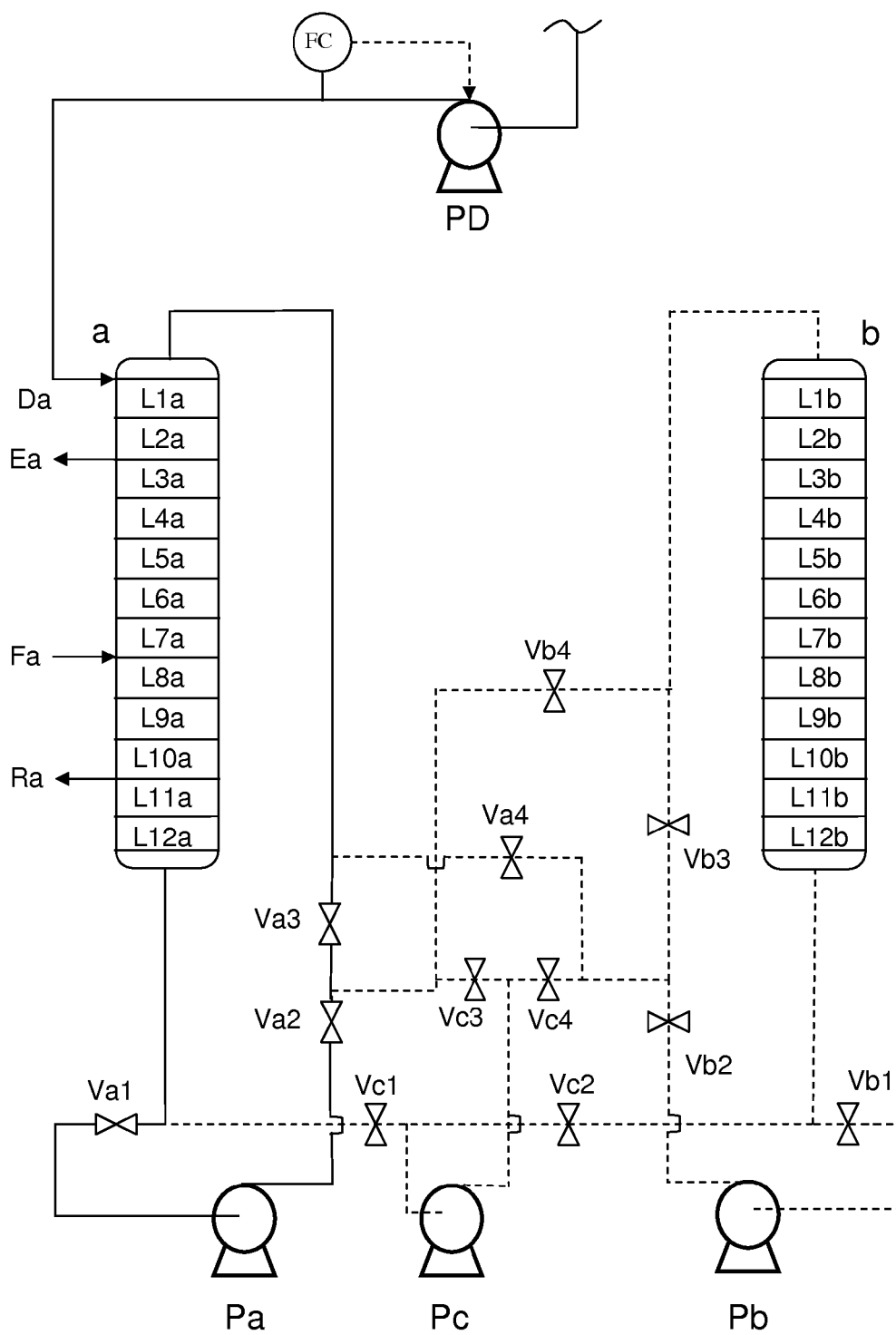

FIG. 4 represents the device of the invention, constituted by two adsorbers (a) and b) each with 12 beds (L1a to L12a for adsorber a), and L1b to L12b for adsorber b), functioning in "maintenance" mode. The two adsorbers are decoupled and only adsorber a) follows a 12-step cycle.

BRIEF DESCRIPTION OF THE INVENTION

The present invention can be defined as a high flexibility process for the SCC (simulated counter-current) separation of xylenes, since the flow rate of treated feed, with respect to a reference run corresponding to 100%, extends to either side, from an "intermediate productivity" run of 50% to 100% up to a run termed "high productivity" from 100% to 150%. In addition, a "maintenance" run can be used to process a feed flow rate in the range 50% to 75% of the reference feed flow rate, with a single adsorber, thus allowing "maintenance" of the second adsorber.

The process of the present invention produces an extract and a raffinate from a feed constituted by a mixture of xylenes, using a set of two adsorbers denoted a) and b), each adsorber comprising 12 beds of solid adsorbent, these two adsorbers being capable of being associated in 3 different manners, as a function of the feed flow rate and any maintenance operation on one of the adsorbers:

the "high productivity" mode can be used to treat a feed flow rate in the range 100% to 150% of the reference feed flow rate. The two adsorbers a) and b) are associated in parallel, i.e. the streams from the bottoms of the two adsorbers are orientated to move towards the head of the adsorber from which they derive, the stream from the bottom of adsorber a) being recycled to the head of said adsorber a), and the stream from the bottom of adsorber b) being recycled to the head of said adsorber b). The valves are opened and closed to allow operation in accordance with this run; the sequence is given in the detailed description made with reference to FIG. 3;

the "intermediate productivity" mode can be used to treat a feed flow rate in the range 50% to 100% of the reference feed flow rate. The adsorbers a) and b) are associated in series, i.e. the principal stream moves from the bottom of the first adsorber a) towards the head of the second adsorber b) and from the bottom of the second adsorber b) towards the head of the first adsorber a). The valves are opened and closed to allow operation in accordance with this run; the function is given in the detailed description made with reference to FIG. 2;

the "maintenance" mode can be used to treat a feed flow rate in the range 50% to 75% of the reference feed flow rate. The two adsorbers are decoupled, the process functioning with a single adsorber, a) or b) ("of" is exclusive). The stream from the bottom of the adsorber used (a) or b) is orientated to move towards the head of said adsorber. The valves are opened and closed to allow operation in accordance with this run; the function is given in the detailed description made with reference to FIG. 4.

The reference feed flow rate (100%) is defined as the maximum flow of feed that can be treated in a unit of the invention in the "intermediate productivity" mode (i.e. in a mode equivalent to a single 24-bed cycle) such that the mean linear velocity over the assembly of 24 beds with respect to the empty adsorber is equal to 1.4 cm/s.

Each adsorber is divided into 4 zones defined as follows:
zone 1: para-xylene desorption zone, included between the injection of desorbant D and the removal of extract E;
zone 2: desorption zone for isomers of para-xylene, included between the removal of the extract E and the injection of the feed to be fractionated F;

zone 3: para-xylene adsorption zone, included between the injection of the feed and the withdrawal of the raffinate R;

zone 4: zone located between the withdrawal of the raffinate R and the injection of the desorbant D.

In the association of adsorbers a) and b) known as "in parallel", corresponding to the "high productivity" run, all of the feed and desorbant supply streams and extract and raffinate withdrawal streams are doubled up.

In the association of adsorbers a) and b) known as "in series", corresponding to the "intermediate productivity" run, there is one feed supply stream, one desorbant introduction stream, one extract withdrawal stream and one raffinate withdrawal stream.

In the run termed "maintenance", the two adsorbers are completely decoupled; they are no longer associated and only one of the two adsorbers is used.

The SCC separation process of the present invention can accommodate a plurality of derivations or variations corresponding to different distributions of the beds of adsorbent in the various zones.

The term "synchronous cycle" means a cycle in which all of the injection points (feed and desorbant) and withdrawal points (extract and raffinate) are shifted simultaneously and by the same value. The number of beds per zone is thus constant and equal to a whole number.

The term "asynchronous" (or "Varicol" type) cycle means a cycle in which certain injection and withdrawal points are not shifted at the same time as the others. Thus, the number of beds per zone is not constant and a non-integral mean number of beds is obtained for one cycle.

In a first variation of the process of the present invention, in "intermediate productivity" mode, the number of beds per zone is:
zone 1: 5;
zone 2: 9;
zone 3: 7;
zone 4: 3;
this is abbreviated to 5/9/7/3; hereinafter, the number of beds will be given in the order of zones 1, 2, 3 then 4.

In a second variation of the process of the present invention, in "intermediate productivity" mode, the number of beds per zone is 4/10/7/3.

In a first variation of the process of the invention, in "high productivity" mode, each of the adsorbers follows a cycle in which the shifts of the injection and withdrawal points are synchronous; the number of beds per zone for each adsorber is 2/5/3/2.

In a second variation of the process of the invention, in "high productivity" mode, each of the adsorbers follows a cycle in which the shifts of the injection and withdrawal points are asynchronous (Varicol cycle), the mean number of beds per zone for each adsorber over a cycle being:
2.5 (+ or −0.5) beds in zone 1;
4.5 (+ or −0.5) beds in zone 2;
3.5 (+ or −0.5) beds in zone 3;
1.5 (+ or −0.5) beds in zone 4.

In a third variation of the process of the invention, in "high productivity" mode, one of the adsorbers follows a cycle in which the shift of the injection and withdrawal points are synchronous, and the other adsorber follows a cycle in which the shift of the injection and withdrawal points are asynchronous, the number of beds per zone for the adsorber following a synchronous cycle being 2/5/3/2, and the mean number of beds per zone for the adsorber over a cycle following a "Varicol" cycle being:
2.5 (+ or −0.5) beds in zone 1;
4.5 (+ or −0.5) beds in zone 2;
3.5 (+ or −0.5) beds in zone 3;
1.5 (+ or −0.5) beds in zone 4.

In a first variation of the process of the invention in "maintenance" mode, the adsorber used follows a cycle in which the shifts of the injection and withdrawal points are synchronous, the number of beds per zone being 2/5/3/2.

In a second variation of the process of the invention in "maintenance" mode, the adsorber used follows a cycle in which the shifts of the injection and withdrawal points are asynchronous, the mean number of beds per zone of a cycle being:
2.5 (+ or −0.5) beds in zone 1;
4.5 (+ or −0.5) beds in zone 2;
3.5 (+ or −0.5) beds in zone 3;
1.5 (+ or −0.5) beds in zone 4.

The simulated counter-current separation process of the present invention generally uses the following operating conditions in the adsorption step:
temperature 100° C. to 250° C., preferably 120° C. to 180° C.;
pressure in the range from the bubble pressure of the xylenes at the temperature of the process to $30 \times 10^5$ Pa;
ratio of desorbant flow rate to feed flow rate: 0.7 to 2.5;
recycle ratio 2.5 to 12, preferably 3.5 to 6; the recycle ratio is defined as the ratio between the mean flow rate flowing in the various beds of the adsorber and the flow rate of feed injection into that adsorber;
the duration of the cycle followed by the adsorbers is in the range 14 to 30 minutes, preferably in the range 18 to 23 minutes;
the mean linear velocity of the liquid stream with respect to the empty reactor is in the range 0.7 cm/s to 1.4 cm/s, preferably in the range 0.85 cm/s to 1.1 cm/s;
the liquid phase water content is kept to a quantity in the range 50 to 140 ppm (by weight), preferably in the range 80 to 120 ppm (by weight).

The xylene separation process of the present invention may in principal be applied to the separation of any of the isomers of xylene, but is most particularly suitable for the production of para-xylene in a purity of more than 99.7% by weight.

DETAILED DESCRIPTION OF THE INVENTION

The present invention concerns a process for the separation of para-xylene from a feed F essentially comprising para-xylene and its aromatic C8 isomers, constituted by two adsorbers, characterized in that it can function in three functional modes known as a "high productivity", "intermediate productivity" and a "maintenance" mode, the process of the invention also being characterized by the criteria for swinging from one functional mode to another, these swings being conditioned by the feed flow rate for the feed to be treated and any "maintenance" operations on one adsorber. The three functional modes are as follows:

the "intermediate productivity" mode can be used to treat a feed flow rate in the range 50% to 100% of the reference feed flow rate of the unit. This mode consists of operating the beds of the two adsorbers together in a single SCC cycle (in series configuration). In particular, this mode means that operation of the SCC can be continued despite a partial degradation of the solid adsorbent (degradation may be a consequence of poor operation or the age of the solid adsorbent);

the "high productivity" mode can be used to treat a feed flow rate of more than 100% of the reference feed flow rate for the unit. In this mode, the two adsorbers each follow a SCC cycle independently of each other (known as a parallel configuration), the various streams (of feed, desorbant, extract and raffinate) are all divided into two in order to supply and be withdrawn from the two adsorbers simultaneously (one stream of feed, of desorbant, of raffinate and of extract per adsorber);

the "maintenance" mode can be used to treat a feed flow rate in the range 50% to 75% of the reference feed flow rate of the unit. This mode consists of operating just one of the two adsorbers, thereby allowing the second adsorber to be maintained without it being necessary to stop production completely, but simply to reduce productivity.

The reference feed flow rate is defined as the maximum feed flow rate that can be treated in a unit of the invention in the "intermediate productivity" mode, i.e. in a mode equivalent to a single 24-bed cycle, such that the mean linear velocity of the liquid stream inside the adsorbers, with respect to the empty adsorber, is equal to 1.4 cm/s.

The adsorbers each contain twelve beds separated by plates Pi with a chamber for distribution and/or extraction of fluids in or from the various beds of adsorbent, and programmed means for sequential distribution and extraction of fluids.

Preferably, in the process of the invention, a plurality of programmed on-off valves for supply or withdrawal of fluids are provided, these valves typically being located in the immediate vicinity of the corresponding plate, and for each plate Pi comprising at least 4 programmed 2-way on-off valves respectively for the 2 supplies of fluids F and D and the 2 withdrawals of fluids E and R The process of the invention is more particularly constituted by one or two feed pump(s) and two feed flow rate regulating means (one per adsorber), one or two desorbant pumps and two desorbant flow rate regulating means (one per adsorber), two extract flow rate regulating means (one per adsorber), two raffinate flow rate regulating means (one per adsorber), and two recirculating pumps (one per adsorber).

Downstream of the SCC, a single desorbant recycling loop is necessary. It is primarily composed of at least one column for distillation of the extract, preferably two extract distillation columns, and at least one raffinate distillation column.

The process of the invention, composed of two adsorbers, may be controlled by a single automated means that can independently process the two cycles of the two adsorbers.

The process further possesses:
a single pump replacing the feed supply pump(s) and a single pump replacing the desorbant supply pump(s);
a single replacement recirculating pump (Pc), this single replacement pump having the capacity to be used either in replacement of the recirculation pump (Pa) used on the first adsorber a), or in replacement of the recirculation pump (Pb) used on the second adsorber b). When the pump Pc is used in replacement of the pump Pa, the valves Va1 and Va2 are closed, and the valves Vc1 and Vc3 are opened (valves Vc2 and Vc4 being closed). When the pump Pc is used in replacement of the pump Pb, the valves Vb1 and Vb2 are closed and the valves Vc2 and Vc4 are opened (valves Vc1 and Vc3 being closed);
a single automated control device for the two adsorbers;
a single in-line device for analysing concentrations within the adsorbers. Such devices are described in particular in patent FR 2 942 879.

Figure 1:
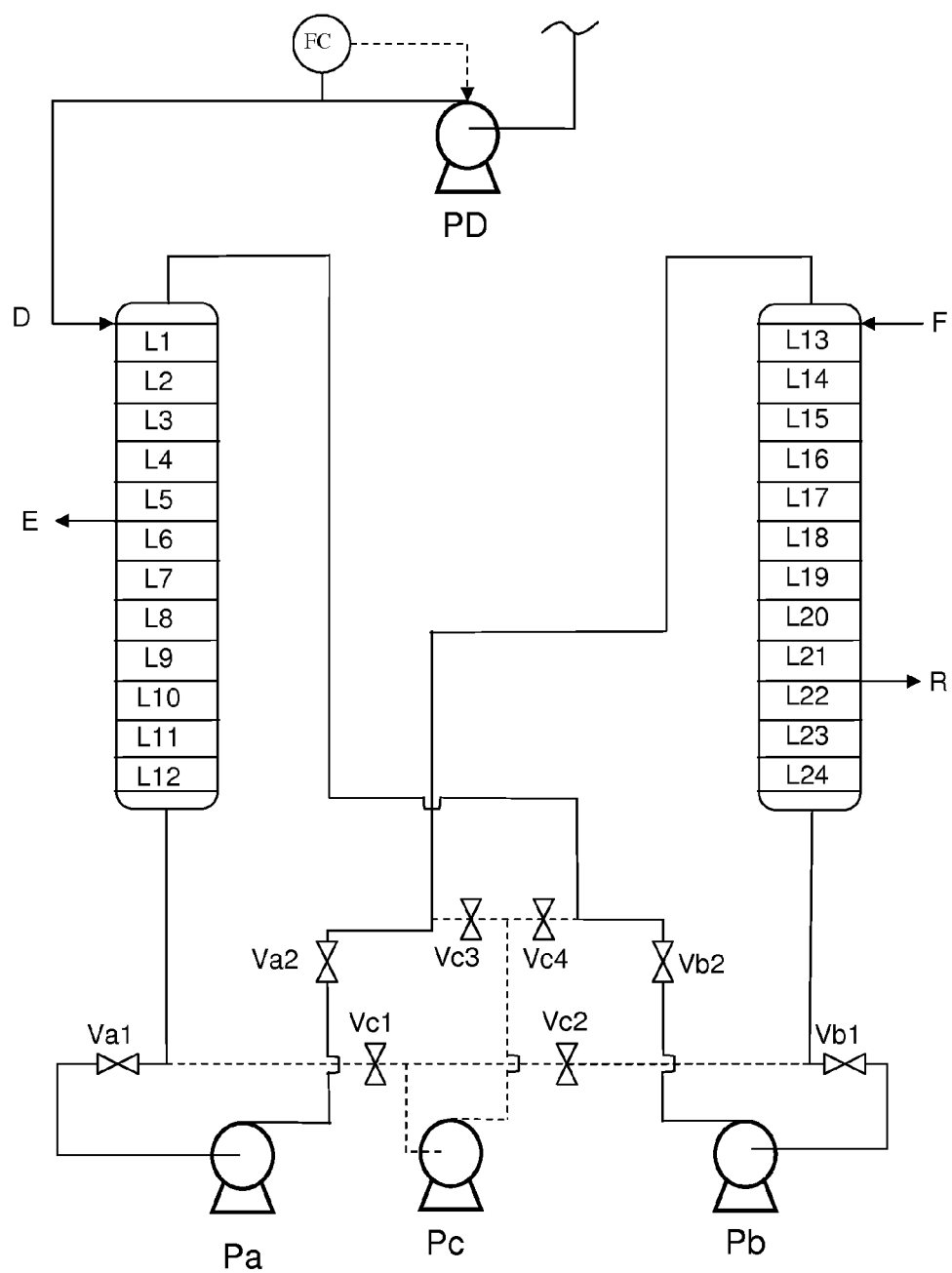
FIG. 1 represents the prior art process comprising two twelve-bed adsorbers each associated in series. There is one feed injection point (F), one desorbant introduction point (D), one extract withdrawal point (E) and one raffinate withdrawal point (R).
Figure 2:
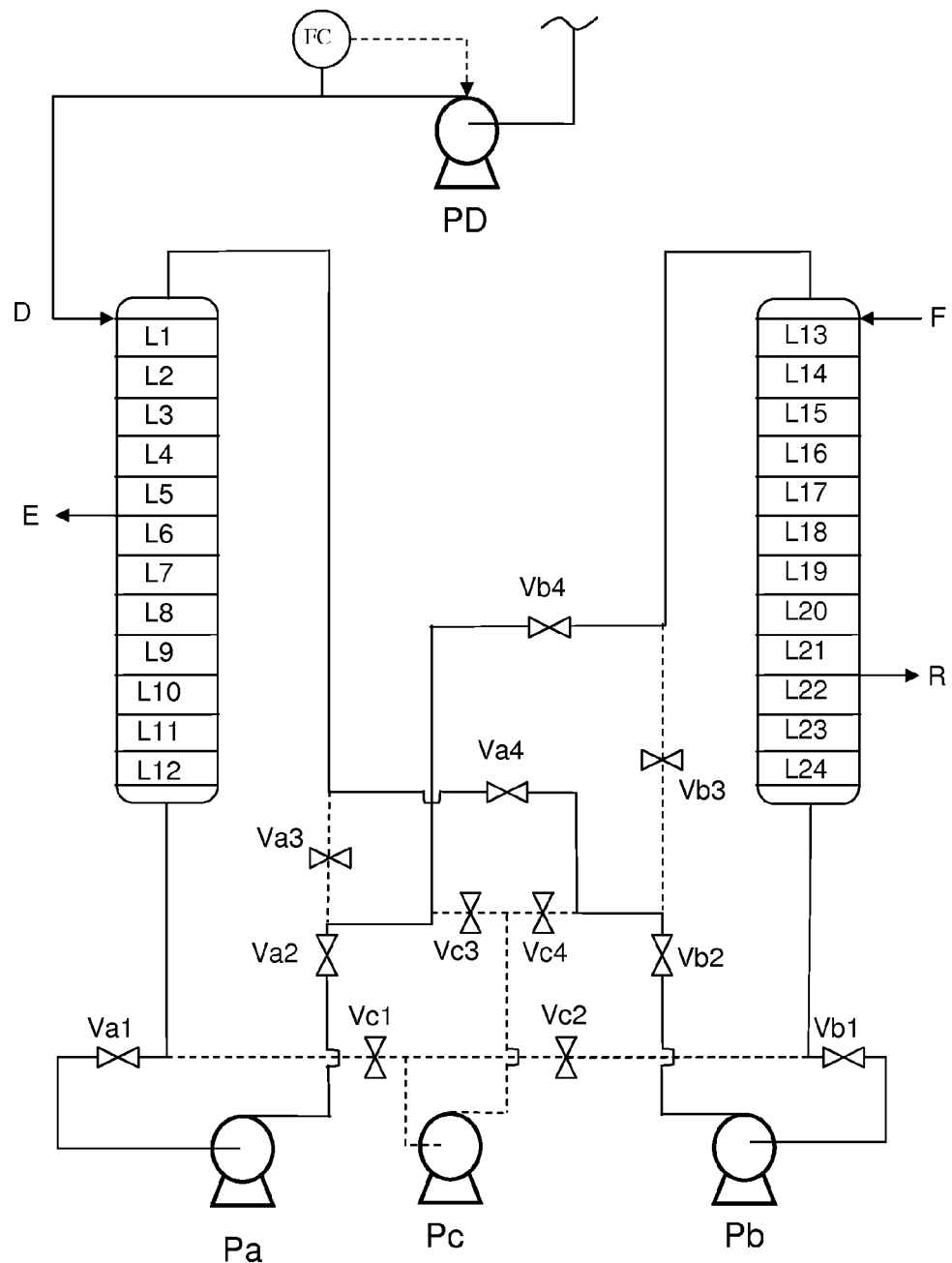
FIG. 2 represents the device of the invention, constituted by two adsorbers each with 12 beds, i.e. a total of 24 beds (L1 to L24), functioning in "intermediate productivity" mode.

In "intermediate productivity" mode, the principal stream moves from the bottom of the first adsorber towards the head of the second adsorber and from the bottom of the second adsorber towards the head of the first adsorber, as can be seen in FIG. 2. To this end, the valves Va1, Va2, Va4, Vb1, Vb2 and Vb4 are opened, while the valves Va3 and Vb3 are closed.

In "high productivity" mode, the streams from the bottoms of the two adsorbers are orientated so that they move towards the head of the adsorber from which they derive, as can be seen in FIG. 3. The bottom stream from adsorber a) is recycled towards the head of said adsorber a) and the bottom stream from adsorber b) is recycled towards the head of said adsorber b). To this end, the valves Va1, Va2, Va3, Vb1, Vb2 and Vb3 are opened, while the valves Va4 and Vb4 are closed.

In "maintenance" mode, the stream from the bottom of the adsorber used is orientated to move towards the head of the adsorber it has just left.

When the adsorber a) is used, the bottom stream from adsorber a) is recycled towards the head of said adsorption a) as can be seen in FIG. 4. To this end, valves Va1, Va2 and Va3 are open, while valve Va4 and the set of valves Vb1 to Vb4 are closed. Similarly, when the adsorber b) is used, the bottom stream from adsorber b) is recycled towards the head of said adsorber b). To this end, valves Vb1, Vb2 and Vb3 are open while valve Vb4 and the set of valves Va1 to Va4 are closed.

The four chromatographic zones are defined as follows:
zone 1: para-xylene desorption zone, included between the injection of desorbant D and the removal of extract E;
zone 2: desorption zone for isomers of para-xylene, included between the removal of the extract E and the injection of the feed to be fractionated F;
zone 3: para-xylene adsorption zone, included between the injection of the feed and the withdrawal of the raffinate R;
zone 4: zone located between the withdrawal of the raffinate R and the injection of the desorbant D.

When functioning in "intermediate productivity" mode, there are two variations in the process of the invention for the distribution of the adsorbent beds in the various chromatographic zones.

In the first variation of the "intermediate productivity" mode of the process of the invention, the shifts of the various injection or withdrawal points are simultaneous, and the beds of the assembly of two adsorbers are distributed in the various zones in the following manner:
5 beds in zone 1;
9 beds in zone 2;
7 beds in zone 3;
3 beds in zone 4.

In the second variation of the "intermediate productivity" mode of the process of the invention, the shifts of the various injection or withdrawal points are simultaneous, the beds of the assembly of two adsorbers are distributed in the various zones in the following manner:
4 beds in zone 1;
10 beds in zone 2;
7 beds in zone 3;
3 beds in zone 4.

In "high productivity" mode, the interstitial speeds within the adsorbent beds are different from those within the beds in "intermediate productivity" mode. The ratio between the interstitial velocity in "intermediate productivity" mode and the interstitial velocity in "high productivity" mode in a given zone is equal to twice the ratio between the flow rate of the feed treated by the process in "intermediate productivity" mode and the sum of the two feed flow rates (one flow rate per adsorber) treated by the process in "high productivity" mode (plus or minus 10%).

The switch period in "high productivity" mode is equal to the switch time of the "intermediate productivity" mode divided by the mean ratio over all of the zones between the interstitial velocity in "high productivity" mode and the interstitial velocity in "intermediate productivity" mode (plus or minus 10%).

In addition, the length of each zone of the SCC in "high productivity" mode is equal to half the length of the same zone in "intermediate productivity" mode plus or minus 30%. In order to obtain non-integral zone lengths, the shifts of the injection and withdrawal points do not have to be simultaneous, as disclosed in U.S. Pat. No. 6,136,198. The term "zone length" means the mean number of beds in the zone over one cycle. During "high productivity" mode production, the process of the invention has three variations concerning the distribution of the beds of adsorbent in the various chromatographic zones of each of the adsorbers.

In the first variation of the "high productivity" mode of the process of the invention, the shifts of the various injection or withdrawal points are simultaneous; the beds of each of the two adsorbers are distributed in the various zones as follows:
 2 beds in zone 1;
 5 beds in zone 2;
 3 beds in zone 3;
 2 beds in zone 4.

In the second variation of the "high productivity" mode of the process of the invention, for one of the adsorbers, the shifts of the 2 injection points and the 2 withdrawal points are simultaneous, the 12 beds of the adsorber being distributed in the 4 chromatographic zones as follows:
 2 beds in zone 1;
 5 beds in zone 2;
 3 beds in zone 3;
 2 beds in zone 4.
and for the other adsorber, the shifts of the 2 injection points and the 2 withdrawal points are not simultaneous, so as to obtain numbers of beds per zone which are not whole numbers on average over a cycle; for this adsorber, the numbers of beds per zone are as follows:
 2.5 (+ or −0.5) beds in zone 1;
 4.5 (+ or −0.5) beds in zone 2;
 3.5 (+ or −0.5) beds in zone 3;
 1.5 (+ or −0.5) beds in zone 4.

In the third variation of the "high productivity" mode of the process of the invention, for each of the adsorbers, the shifts of the 2 injection points and the second withdrawal points are not simultaneous in order to obtain mean numbers of beds per zone which are not whole numbers over a cycle; for each of these adsorbers, the numbers of beds per zone are as follows:
 2.5 (+ or −0.5) beds in zone 1;
 4.5 (+ or −0.5) beds in zone 2;
 3.5 (+ or −0.5) beds in zone 3;
 1.5 (+ or −0.5) beds in zone 4.

In "maintenance" mode, the interstitial velocities in the beds of adsorbent are different from those in the beds in "intermediate productivity" mode. The ratio between the interstitial velocity in "intermediate productivity" mode and the interstitial velocity in "maintenance" mode in a given zone is equal to the ratio between the feed flow rate treated by the process in "intermediate productivity" mode and the feed flow rate treated by the process in "maintenance" mode (plus or minus 10%).

In addition, the switch period in "maintenance" mode is equal to the switch time of the "intermediate productivity" mode divided by the mean ratio over all of the zones between the interstitial velocity in "maintenance" mode and the interstitial velocity in "intermediate productivity" mode (plus or minus 10%).

The length of each zone of the SCC in "maintenance" mode is equal to half the length of the same zone in "intermediate productivity" mode plus or minus 30%. In order to obtain non-integral zone lengths, the shifts of the injection and withdrawal points do not have to be simultaneous, as disclosed in U.S. Pat. No. 6,136,198.

During operation in "maintenance" mode, the process of the invention may have two variations for the distribution of the beds of adsorbent in the various chromatographic zones of the single adsorber used.

In the first variation of the "maintenance" mode of the process of the invention, the shifts of the various injection or withdrawal points are simultaneous; the beds of the adsorber used are distributed in the various zones as follows:
 2 beds in zone 1;
 5 beds in zone 2;
 3 beds in zone 3;
 2 beds in zone 4.

In the second variation of the "maintenance" mode of the process of the invention, the shifts of the 2 injection points and the 2 withdrawal points are not simultaneous, in order to obtain mean numbers of beds per zone which are not whole numbers during a cycle, the numbers of beds per zone for the adsorber in use being as follows:
 2.5 (+ or −0.5) beds in zone 1;
 4.5 (+ or −0.5) beds in zone 2;
 3.5 (+ or −0.5) beds in zone 3;
 1.5 (+ or −0.5) beds in zone 4.

The process of the present invention can be used to obtain a para-xylene yield of more than 90%, preferably more than 95%, and more preferably more than 98%.

The productivity achieved in the process of the invention is in the range 20 kg to 180 kg of para-xylene per hour per $m^3$ of bed of adsorbent, and preferably in the range 35 kg to 140 kg of para-xylene per hour per $m^3$ of bed of adsorbent.

In accordance with one characteristic of the process, the operating conditions of the adsorption step are as follows:
 temperature 100° C. to 250° C., preferably 120° C. to 180° C.;
 pressure in the range from the bubble pressure of the xylenes at the temperature of the process to $30 \times 10^5$ Pa;
 ratio of desorbant flow rate to feed flow rate: 0.7 to 2.5;
 recycle ratio 2.5 to 12, preferably 3.5 to 6; the recycle ratio is defined as the ratio between the mean flow rate flowing in the various beds of the adsorber and the flow rate of feed injection into that adsorber;
 the duration of the cycle followed by the adsorbers is in the range 14 to 60 minutes;
 the mean linear velocity of the liquid stream with respect to the empty reactor is in the range 0.7 cm/s to 1.4 cm/s.

During operation in "high productivity" mode or in "maintenance" mode, the water content in the adsorbers is regulated to a value in the range +5 ppm to +40 ppm by weight above the value regulated during operation in "intermediate productivity" mode. Preferably, this water content is regulated to between +10 ppm and +25 ppm above the value regulated during operation in "intermediate productivity" mode. It has in fact surprisingly been observed that there is an optimized range for the water content within the adsorbers which depends on the selected operational mode for the process of the invention.

Any means that can regulate the water content in the adsorbers may be used in the process of the invention. The preferred means for regulating said water content is injecting water continuously into the streams supplying the adsorber or adsorbers as described in FR 2 757 507.

EXAMPLES

The invention will be better understood from the two examples below.

Example 1

In Accordance with the Prior Art

Consider a SCC unit constituted by 24 beds with a length of 1.1 m and an internal radius of 1.05 m, with a feed injection, a desorbant injection, an extract withdrawal and a raffinate withdrawal.

The adsorbent employed was a zeolitic BaX type solid and the desorbant was para-diethylbenzene. The temperature was 175° C. and the pressure was 15 bars. The water content was 95 ppm (by weight).

The feed was composed of 21.6% para-xylene, 20.8% ortho-xylene, 47.9% meta-xylene and 9.7% ethylbenzene.

The SCC unit was constituted by 24 beds separated by distributor plates. An injection network and a withdrawal network were associated with each distributor plate. The rinsing device used was the modulated bypass fluid flow rate device as described in patent WO 2010/020715. The synchronicity was 100% in each zone.

Intermediate Productivity Case:

The shifts for the various injection and withdrawal points were simultaneous. The beds were distributed in the 4 chromatographic zones in accordance with the configuration: 5/9/7/3.

The feed and desorbant injection flow rates (defined by assuming a reference temperature of 40° C.) were as follows:
  0.637 m³/min for the feed;
  0.805 m³/min for the desorbant.

In addition, the flow rate for zone 4 was 1.963 m³/min and the extract withdrawal flow rate was 0.414 m³/min. The switch period employed was 68.0 seconds.

By simulation, a para-xylene purity of 99.86% was obtained with a yield of para-xylene of 98.4%, and with a productivity of 75.5 $kg_{PX} \cdot h^{-1} \cdot m^{-3}$ (the index PX indicates that the productivity is expressed in kg of para-xylene).

The minimum for the feed flow rate was obtained by assuming that the feed and desorbant injection flow rates (defined using a reference temperature of 40° C.) were as follows:
  0.316 m³/min for the feed;
  0.400 m³/min for the desorbant.

In addition, the flow rate for zone 4 was 0.975 m³/min and the extract withdrawal flow rate was 0.206 m³/min. The switch period employed was 137.0 seconds.

By simulation, a para-xylene purity of 99.86% was obtained with a yield of para-xylene of 97.3%, and with a productivity of 37.1 $kg_{PX} \cdot h^{-1} \cdot m^{-3}$.

High Productivity Case:

It was not possible to increase the flow rates obtained for intermediate productivity because of the pressure drops in the adsorbers and the mechanical behaviour of the adsorbent solid and the internal devices.

Maintenance on an Adsorber:

During maintenance, such as replacement of the solid adsorbent, for example, the whole SCC unit had to be stopped and there was no para-xylene production.

Example 2

In Accordance with the Invention

Consider a SCC unit constituted by two adsorbers each with 12 beds. Each bed had a length of 1.1 m and an internal radius of 1.05 m.

The adsorbent employed was a zeolitic BaX type solid and the desorbant was para-diethylbenzene. The temperature was 175° C. and the pressure was 15 bars.

The feed was composed of 21.6% para-xylene, 20.8% ortho-xylene, 47.9% meta-xylene and 9.7% ethylbenzene.

Each adsorber was constituted by 12 beds separated by distributor plates. An injection network and a withdrawal network corresponded to each distributor plate. The rinsing device used was the modulated bypass fluid flow rate device as described in patent WO 2010/020715. The synchronicity was 100% in each zone.

Intermediate Productivity Case:

The shifts for the various injection and withdrawal points were simultaneous. The beds were distributed in the 4 chromatographic zones in accordance with the configuration 5/9/7/3.

The feed and desorbant injection flow rates (defined by assuming a reference temperature of 40° C.) were as follows:
  0.637 m³/min for the feed;
  0.805 m³/min for the desorbant.

In addition, the flow rate for zone 4 was 1.963 m³/min and the extract withdrawal flow rate was 0.414 m³/min. The switch period employed was 68.0 seconds. The water content was 95 ppm (by weight).

By simulation, a para-xylene purity of 99.86% was obtained with a yield of para-xylene of 98.4%, and with a productivity of 75.5 $kg_{PX} \cdot h^{-1} \cdot m^{-3}$.

The minimum of the treated feed flow rate was obtained by assuming that the feed and desorbant injection flow rates (defined using a reference temperature of 40° C.) were as follows:
  0.316 m³/min for the feed;
  0.400 m³/min for the desorbant.

In addition, the flow rate for zone 4 was 0.975 m³/min and the extract withdrawal flow rate was 0.206 m³/min. The switch period employed was 137.0 seconds.

By simulation, a para-xylene purity of 99.86% was obtained with a yield of para-xylene of 97.3%, and with a productivity of 37.1 $kg_{PX} \cdot h^{-1} \cdot m^{-3}$.

High Productivity Case:

Each adsorber followed a cycle independently of the cycle of the other adsorber.

For each of the adsorbers, the shifts of the various injection and withdrawal points were simultaneous. In each of the adsorbers, the beds were distributed into 4 chromatographic zones in accordance with the configuration:
  2/5/3/2

For each of the two adsorbers, the feed and desorbant injection flow rates (defined by assuming a reference temperature of 40° C.) were as follows:
  0.464 m³/min for the feed;
  0.627 m³/min for the desorbant.

In addition, the flow rate for zone 4 was 1.412 m³/min and the extract withdrawal flow rate was 0.360 m³/min. The switch period employed was 91.1 seconds. The water content was 110 ppm (by weight).

By simulation, a para-xylene purity of 99.71% was obtained with a yield of para-xylene of 97.03%, and with a productivity of 108.5 $kg_{PX} \cdot h^{-1} \cdot m^{-3}$, considering the whole unit constituted by the two adsorbers.

Maintenance on One Adsorber:

The adsorber which was not being maintained followed a 12 bed SCC cycle, with simultaneous shifts of the various injection and withdrawal points. The beds were distributed into 4 chromatographic zones in accordance with the configuration:

2/5/3/2

The feed and desorbant injection flow rates (defined by assuming a reference temperature of 40° C.) were as follows:

0.464 m³/min for the feed;

0.627 m³/min for the desorbant.

In addition, for each of the adsorbers, the flow rate for zone 4 was 1.412 m³/min and the extract withdrawal flow rate was 0.360 m³/min. The switch period employed was 91.1 seconds. The water content was 110 ppm (by weight).

By simulation, a para-xylene purity of 99.71% was obtained with a yield of para-xylene of 97.03%, and with a productivity of 54.2 $kg_{PX} \cdot h^{-1} \cdot m^3$, considering the whole unit constituted by the two adsorbers.

These examples provide a good illustration of the advantages of the process of the invention which has the same performance as the prior art process for the low and intermediate productivities, but in addition can obtain higher productivities. The process of the invention can also be used to maintain para-xylene production during maintenance operations on one of the adsorbers, in contrast to the prior art process.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 11/02.604, filed Aug. 26, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the separation of xylenes producing an extract and a raffinate from a feed constituted by a mixture of xylenes, and operating in simulated counter-current using a series of two adsorbers denoted a) and b) each comprising 12 beds of solid adsorbent, each adsorber being divided into 4 zones defined as follows:

zone 1: para-xylene desorption zone, included between the injection of desorbant D and the removal of extract E;

zone 2: desorption zone for isomers of para-xylene, included between the removal of the extract E and the injection of the feed to be fractionated F;

zone 3: para-xylene adsorption zone, included between the injection of the feed and the withdrawal of the raffinate R;

zone 4: zone located between the withdrawal of the raffinate R and the injection of the desorbant D;

and the two adsorbers being able to generate in 3 different modes as a function of the flow rate of the feed to be treated and any maintenance operation on one of the adsorbers:

in high productivity mode, from 100% to 150%, the two adsorbers are associated in parallel, where the streams from the bottoms of the two adsorbers are orientated to move towards the head of the adsorber from which they derive, the stream from the bottom of adsorber a) being recycled to the head of said adsorber a) and the stream from the bottom of adsorber b) being recycled to the head of said adsorber b);

in intermediate productivity mode, 50% to 100%, the adsorbers are associated in series, where the principal stream moves from the bottom of the first adsorber a) towards the head of the second adsorber b) and from the bottom of the second adsorber b) towards the head of the first adsorber a);

in maintenance mode, 50% to 75%, the two adsorbers are decoupled, the process operating with a single adsorber, the stream from the bottom of the adsorber used (a) or b) being orientated to move towards the head of said adsorber;

the reference feed flow rate 100% being defined as the maximum feed flow rate that can be treated in the unit in intermediate productivity mode such that the mean linear velocity of the liquid stream within the adsorbers with respect to the empty adsorber is equal to 1.4 cm/s.

2. A simulated counter-current separation process according to claim 1, in which in high productivity mode, each adsorber shifts the feed and desorbant introduction points and the extract and raffinate withdrawal points simultaneously, the number of beds per zone being as follows:

zone 1: 2;

zone 2: 5 zone 3: 3 zone 4: 2 which is abbreviated to 2/5/3/2.

3. A simulated counter-current separation process according to claim 1, in which in high productivity mode, one of the adsorbers shifts the feed and desorbant introduction points and the extract and raffinate withdrawal points simultaneously, and the other adsorber is in Varicol type shift mode, the number of beds per zone for the adsorber in simultaneous shift mode being 2/5/3/2 and the mean number of beds per zone for the adsorber in Varicol type shift mode being:

2.5+ or −0.5 beds in zone 1;

4.5+ or −0.5 beds in zone 2;

3.5+ or −0.5 beds in zone 3;

1.5+ or −0.5 beds in zone 4.

4. A simulated counter-current separation process according to claim 1, in which in high productivity mode, the two adsorbers a) and b) shift the feed and desorbant introduction points and the extract and raffinate withdrawal points in Varicol type mode, the mean number of beds per zone being:

2.5+ or −0.5 beds in zone 1;

4.5+ or −0.5 beds in zone 2;

3.5+ or −0.5 beds in zone 3;

1.5+ or −0.5 beds in zone 4.

5. A simulated counter-current separation process according to claim 1, in which in intermediate productivity mode, the two adsorbers a) and shift the feed and desorbant introduction points and the extract and raffinate withdrawal points simultaneously, the number of beds per zone being 5/9/7/3.

6. A simulated counter-current separation process according to claim 1, in which in intermediate productivity mode, the two adsorbers a) and b) shift the feed and desorbant introduction points and the extract and raffinate withdrawal points simultaneously, the number of beds per zone being 4/10/7/3.

7. A simulated counter-current separation process according to claim 1, in which in maintenance mode, the adsorber used shifts the feed and desorbant introduction points and the extract and raffinate withdrawal points simultaneously, the number of beds per zone being 2/5/3/2.

8. A simulated counter-current separation process according to claim 1, in which in maintenance mode, the adsorber used is in Varicol type shift mode for the feed and desorbant introduction points and the extract and raffinate withdrawal points, the number of beds per zone being:
- 2.5+ or −0.5 beds in zone 1;
- 4.5+ or −0.5 beds in zone 2;
- 3.5+ or −0.5 beds in zone 3;
- 1.5+ or −0.5 beds in zone 4.

9. A simulated counter-current separation process according to claim 1, in which the operating conditions for the adsorption step are as follows:
- temperature 100° C. to 250° C.;
- pressure in the range from the bubble pressure of the xylenes at the temperature of the process to $30 \times 10^5$ Pa;
- ratio of desorbant flow rate to feed flow rate: 0.7 to 2.5;
- recycle ratio 2.5 to 12; the recycle ratio is defined as the ratio between the mean flow rate flowing in the various beds of the adsorber and the flow rate of feed injection into that adsorber;
- the duration of the cycle followed by the adsorbers is in the range 14 to 30 minutes;
- the mean linear velocity of the liquid stream with respect to the empty reactor is in the range 0.7 cm/s to 1.4 cm/s;
- the liquid phase water content is kept to a quantity in the range 50 to 140 ppm by weight.

10. A simulated counter-current separation process according to claim 1, in which the water content in the adsorbers in the high productivity mode is regulated to a value in the range +5 ppm to +40 ppm by weight higher than the value regulated during the operation in intermediate productivity mode.

11. A simulated counter-current separation process according to claim 1, in which the water content in the adsorber used in the maintenance mode is regulated to a value in the range +5 ppm to +40 ppm by weight higher, than the value regulated during the operation in intermediate productivity mode.

12. A process for the separation of xylenes according to claim 1, applied to the production of para-xylene in a purity of more than 99.7% by weight.

13. A simulated counter-current separation process according to claim 1, in which the operating conditions for the adsorption step are as follows:
- temperature 120° C. to 180° C.;
- pressure in the range from the bubble pressure of the xylenes at the temperature of the process to $30 \times 10^5$ Pa;
- ratio of desorbant flow rate to feed flow rate: 0.7 to 2.5;
- recycle ratio 3.5 to 6, the recycle ratio is defined as the ratio between the mean flow rate flowing in the various beds of the adsorber and the flow rate of feed injection into that adsorber;
- the duration of the cycle followed by the adsorbers is in the range 18 to 23 minutes
- the mean linear velocity of the liquid stream with respect to the empty reactor is in the range 0.84 cm/s to 1.1 cm/s;
- the liquid phase water content is kept to a quantity in the range 80 to 120 ppm by weight.

14. A simulated counter-current separation process according to claim 1, in which the water content in the adsorbers in the high productivity mode is regulated to a value in the range +10 ppm to +25 ppm by weight higher than the value regulated during the operation in intermediate productivity mode.

15. A simulated counter-current separation process according to claim 1, in which the water content in the adsorbers in the high productivity mode is regulated to a value in the range +10 ppm to +25 ppm by weight higher than the value regulated during the operation in intermediate productivity mode.

* * * * *